United States Patent [19]

Inoue

[11] 4,310,115
[45] Jan. 12, 1982

[54] APPARATUS FOR SUTURING A RECTUM

[75] Inventor: Noboru Inoue, Tokyo, Japan

[73] Assignee: Takasago Medical Industry Co., Ltd., Tokyo, Japan

[21] Appl. No.: 99,506

[22] Filed: Dec. 3, 1979

[30] Foreign Application Priority Data

Dec. 9, 1978 [JP] Japan .................................. 53-152875

[51] Int. Cl.³ ............................................. A61B 17/04
[52] U.S. Cl. ................................. 227/19; 128/334 R; 227/DIG. 1
[58] Field of Search .................... 128/334 R, 326, 325, 128/321, 346; 72/410; 227/19, DIG. 1; 29/243.56

[56] References Cited

U.S. PATENT DOCUMENTS

| | | | |
|---|---|---|---|
| 3,193,165 | 7/1965 | Akhalaya et al. | 227/DIG. 1 A X |
| 3,519,187 | 7/1970 | Kapitanov et al. | 128/334 R X |
| 3,790,572 | 2/1974 | Razgulov et al. | 227/19 |
| 4,047,654 | 9/1977 | Alvarado | 227/DIG. 1 X |

Primary Examiner—Michael H. Thaler
Attorney, Agent, or Firm—Young & Thompson

[57] ABSTRACT

An apparatus of the invention comprises a cylindrical hollow supporting member having a nozzle tip and needle opposing seats, suturing members surrounding the needle opposing seats and having therein needle receiving spaces and pushing members for supplying needles, actuating bars for moving the suturing members, and an adjusting member for operating the actuating bars. The apparatus is useful for connecting a rectum upon removal of the diseased part thereof.

9 Claims, 10 Drawing Figures

4,310,115

APPARATUS FOR SUTURING A RECTUM

BACKGROUND OF THE INVENTION

This invention relates to an apparatus for suturing a rectum, which is useful for connecting the rectum upon removal of the diseased parts thereof.

The diseased parts, such as piles and rectal cancers, found near the anus in the rectum are sometimes removed without laparotomy by for example, pulling out a part of the rectum from the anus in the reversed state, positioning the diseased part to be cut off at the tip and cutting off the same after having connected the tract just above that part. In this connecting operation the suturing procedure is usually employed.

Various types of apparatus have hitherto been proposed for such suturing procedure but satisfactory apparatus useful for suturing the rectum, has not heretofore been created, which is readily handled and enables the rapid and smooth suturing.

The inventor has now succeeded in creating an apparatus for directly suturing the diseased part to be pulled out from the rectum before cutting off (including the case of the diseased part being previously cut off) in order to connect the rectum.

Namely, an apparatus comprises a cylindrical hollow supporting member provided with a nozzle tip at its one end and a plurality of needle opposing seats arranged adjacent to the nozzle tip around the suporting member, suturing members opposite to and surrounding the needle seats and annularly spaced apart each other, actuating bars which support the suturing members in relation to the supporting member, and an adjusting member provided at the other end of the supporting member for radially moving the suturing members through the actuating members from and to the needle opposing seats. The suturing apparatus thus constructed provides the convenient suturing operation wherein the supporting member is inserted from its nozzle tip into the pulled-out rectum which is then held between the needle opposing seats and the suturing members and thereafter is sutured with needles supplied from the suturing members.

SUMMARY OF THE INVENTION

Accordingly, the general object of the invention is to provide a convenient apparatus for suturing a rectum rapidly, properly and smoothly while keeping the pulled-out tract in the tubular state, before or after the cutting-off of the diseased part.

The principal object of the invention is to provide an apparatus for suturing a rectum, which comprises a cylindrical hollow supporting member having at its one end a nozzle tip to be inserted into the rectum and being provided with a plurality of needle opposing seats adjacent to the nozzle tip and on the circumference of the supporting member, a plurality of suturing members surrounding the needle opposing seats and annularly spaced apart each other, said suturing members each having therein a plurality of needle receiving spaces radially and a plurality of pushing members slidably inserted into the needle receiving spaces for pushing needles toward the needle opposing seats, actuating bars each being pivoted to the supporting member and connected at its one end to the suturing member for allowing radial movement thereof in relation to the supporting member, and an adjusting member provided at the other end of the supporting member for radially moving the actuating bars through a mechanism arranged within the supporting member.

The invention will be more clearly understood from the following description with reference to the accompanying drawings which are designed to be illustrative only and not limiting, in which:

BRIEF DESCRIPTION OF THE DRAWINGS

FIGS. 6 to 9 are pictorial views in the suturing operation of the apparatus according to the invention wherein FIG. 6 shows the diseased rectum pulled out from the anus;

FIG. 7 is a pictorial view illustrative of the suturing operation after having cut off the diseased part;

FIG. 8 is a pictorial view showing the sutured rectum after it is returned into the body; and FIG. 9 is an enlarged sectional view of the sutured part.

PREFERRED EMBODIMENT OF THE INVENTION

Figure 1:
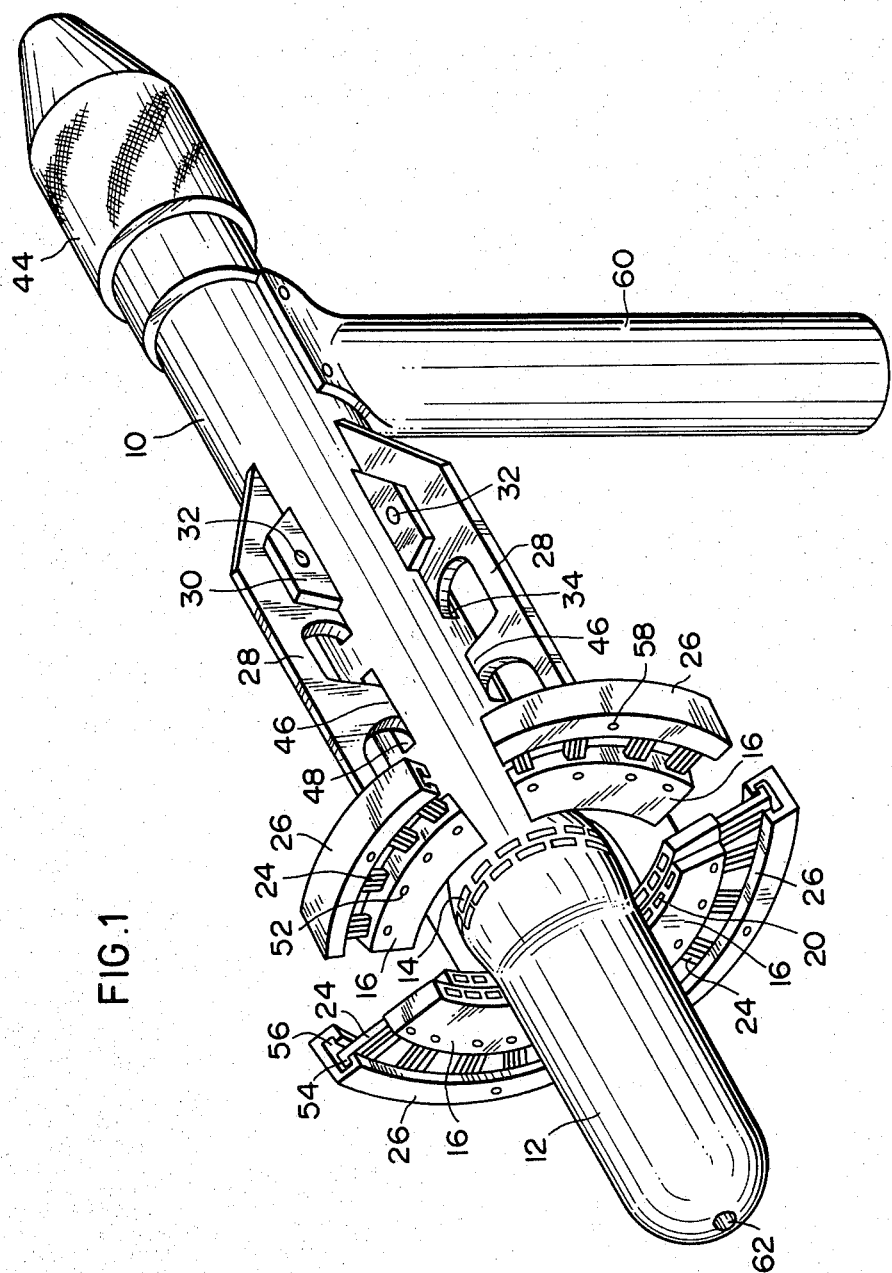
FIG. 1 is a perspective view of the suturing apparatus of one embodiment according to the invention.
Figure 2:
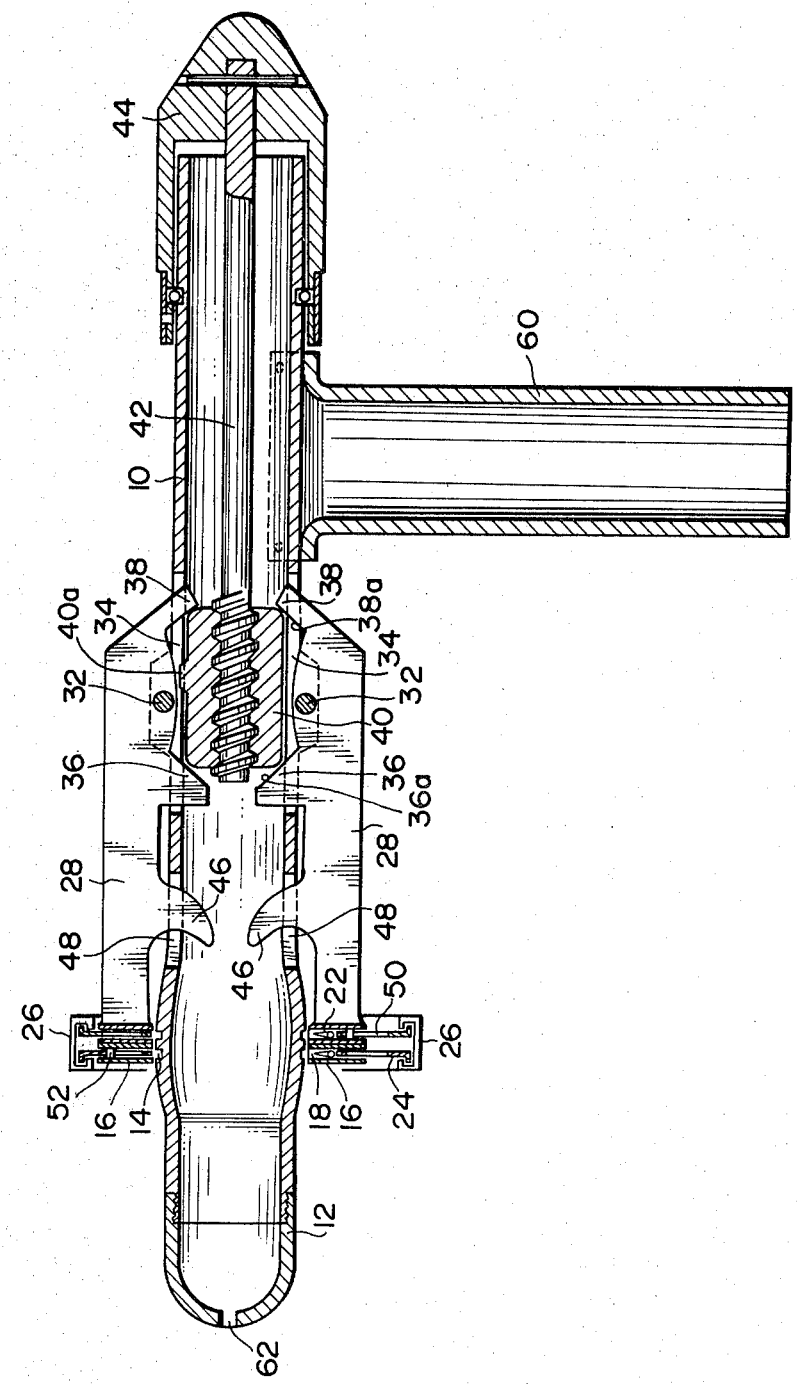
FIG. 2 is a sectional side view of the suturing apparatus shown in FIG. 1.

In FIGS. 1 and 2, the reference numeral 10 represents a cylindrical hollow supporting member which has a nozzle tip 12 at its one end. A plurality of needle opposing seats 14 of a given width are concavely arranged adjacent to the nozzle tip 12 over the whole circumference of the supporting member 10, as best shown in FIG. 1. Around the needle opposing seats 14 of the supporting member 10 are annularly arranged four radially divided suturing members 16 which are provided therein with a plurality of radially arranged needle receiving spaces 18. A plurality of needle outlets 20 communicating with the needle receiving spaces are arranged along the inner circumference of the suturing member 16, while a plurality of pushing members 24 are slidably inserted from the outer circumference of the suturing members 16 into the needle receiving spaces 18 for pushing the needles 22 toward the outlet 20. On the outer ends of the pushing members 24 are mounted four operating members 26 corresponding to the four suturing members 16 for radially and inwardly pushing the pushing members 24, as shown in FIGS. 1 and 2.

Each suturing member 16 is connected to an actuating bar 28 extending longitudinally along the supporting member 10 at its one end. The other end of each actuating bar 28 is pivoted to projecting pieces 30 with a pin 32. As best shown in FIG. 2, projections 36 and 38 having opposite contacting oblique surfaces 36a and 38a are formed at the pivoted end side of the actuating bar 28 and are fitted into a slot 34 of the supporting member 10. Within the hollow supporting member 10, a moving member 40 is located between the projections 36 and 38. The moving member 40 is connected to a threaded shaft 42 which is coaxial to the supporting member 10 and is adjustably moved by turning of a knob 44 provided at the other end of the supporting member 10. As a result, the moving member 40 may be moved forward and backward by the turning of the knob 44, thereby moving the actuating bar 28 and hence the suturing member 16 radially toward and apart from the supporting member 10, as best shown in FIG. 2. Member 40 has a projection 40a thereon, that rides in slot 34 to prevent member 40 from rotating with shaft 42. The actuating bar 28 is preferably provided with a steady rest 46, which is fitted into a slot 48 of the supporting member 10 for preventing radial movement upon operation.

Figure 4A:
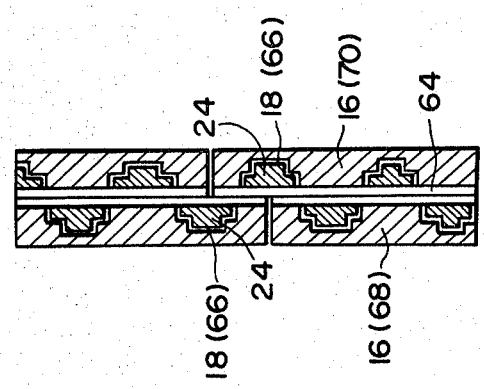
FIG. 4a is a partially sectioned view of one arrangement of the suturing members as shown in FIG. 3.
Figure 4B:
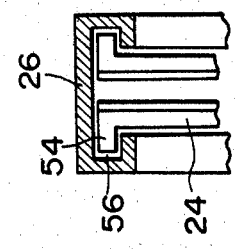
FIG. 4b is a partially sectioned view of an operation member slidably fitted onto the suturing member or pushing member of FIG. 3.
Figure 5:
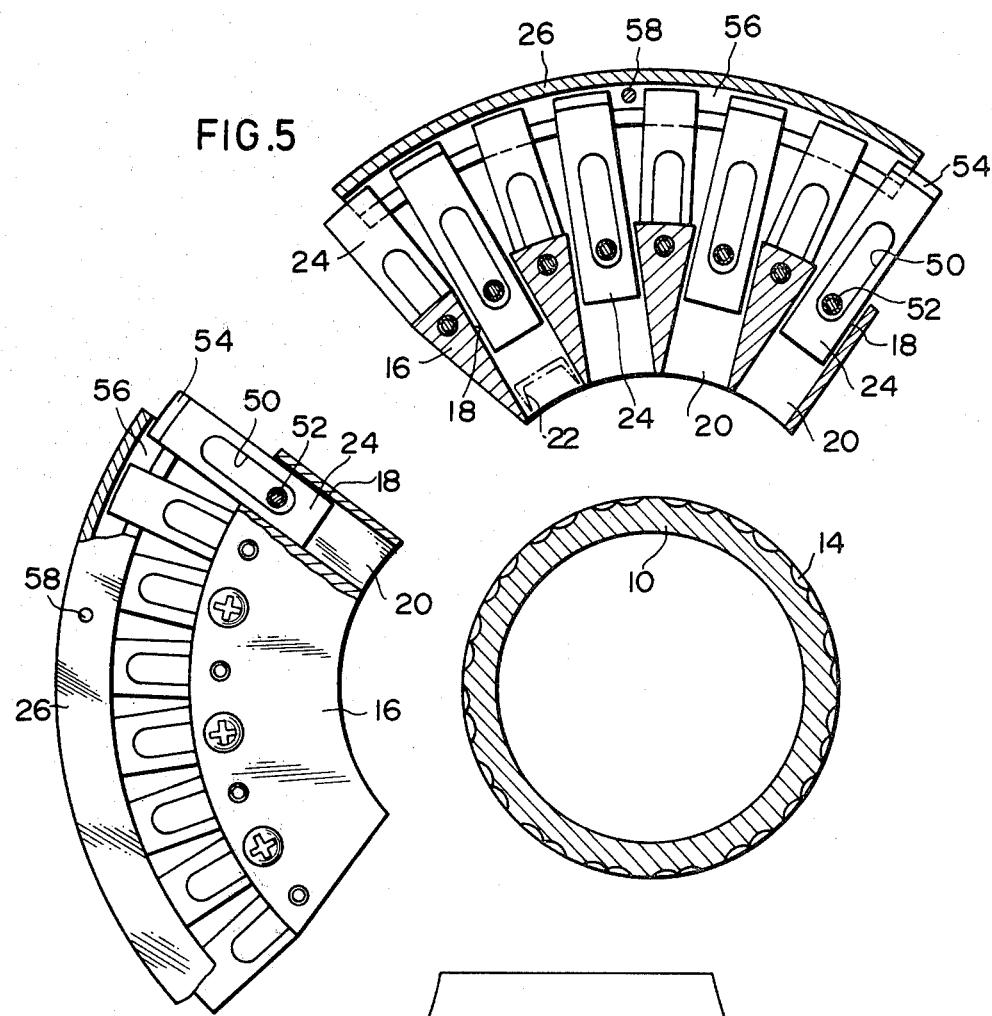
FIG. 5 is a pictorial view in operation of the suturing members shown in FIG. 3.

Now, the most important suturing element of the apparatus according to the invention is described in detail with reference to FIGS. 3 to 5.

Figure 3:
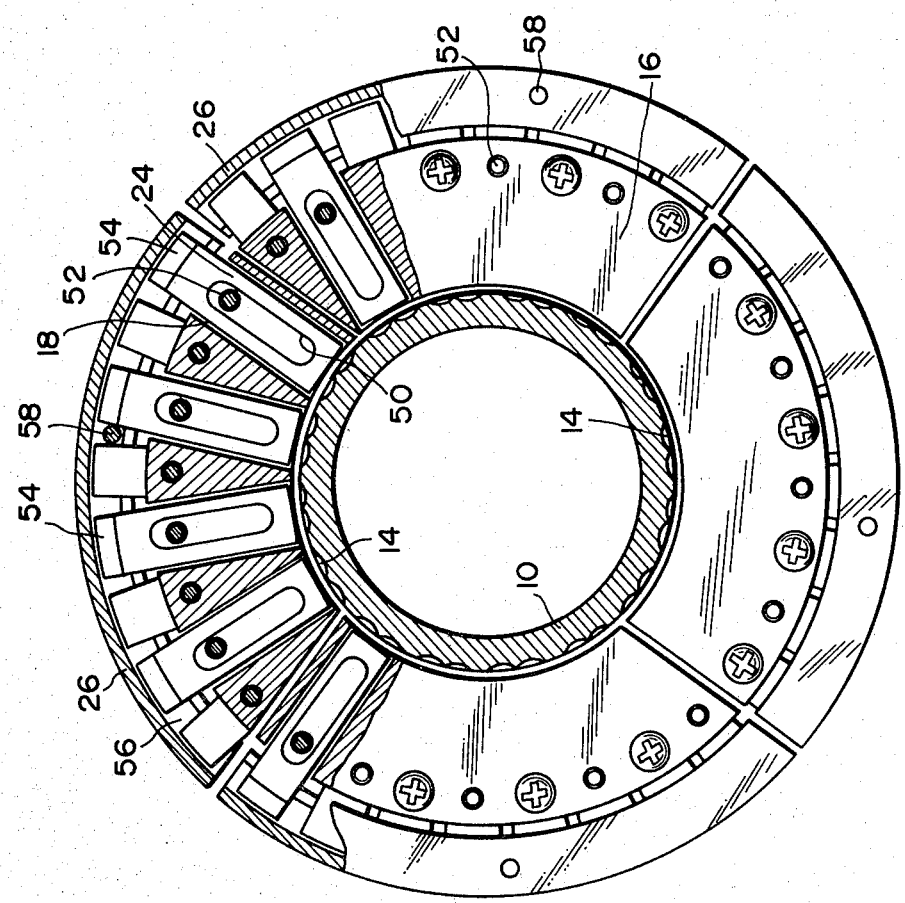
FIG. 3 is a partially sectioned front elevation showing the relation between the suturing members and the needle opposing seats of the apparatus of FIG. 1.

As shown in FIG. 3, the pushing element 24 is pushed into the needle receiving space 18 of the suturing member 16 under pressure of the operating member 26. For this purpose, the pushing member 24 is provided with an elongated hole 50 into which a pin 52 is inserted and thus the pushing member 24 is movably attached to the suturing member 16. The outer edges of the pushing member 24 are formed as bent parts 54, as best shown in FIG. 4b, and are slidably fitted into a dovetail groove 56 of the operating member 26. In accordance with this embodiment, the needle receiving spaces 18 may be doubly and alternately provided for the suturing member 16, as shown in FIG. 4a, wherein the bent parts 54 of each pushing member 24 may be slidably fitted into the dovetail groove, as also shown in FIG. 4b. Thus, the operating member 26 and the pushing member 24 may be jointly and radially moved in relation to the suturing member 16. In order to prevent slipping of the pushing member 24 from the operating member 26, a stop pin 58 is inserted into the dovetail groove 56 and between a pair of adjacent pushing members 24.

In this embodiment, a gripping handle 60 may be provided for the supporting member 10, as shown in FIG. 2. Further, the nozzle tip 12 of the supporting member 10 is preferably provided at its front end with an aperture 62 for washing the inside of the supporting member 10, as also shown in FIG. 2. When the double and alternate needle receiving spaces 18 are provided for the suturing member 16, as shown in FIG. 4a, a partition wall 64 may be arranged between the opposite side walls 68 and 70 each having the needle receiving recess 66, thereby facilitating construction of the suturing member 16. The needle 22 to be used for the apparatus of the invention may be made from a single untwisted and unstranded stainless steel wire in the shape of a staple, as shown in FIG. 5.

The operation of the suturing apparatus according to the invention will be described hereinafter for the removal of the diseased part present near the anus.

Figure 6:
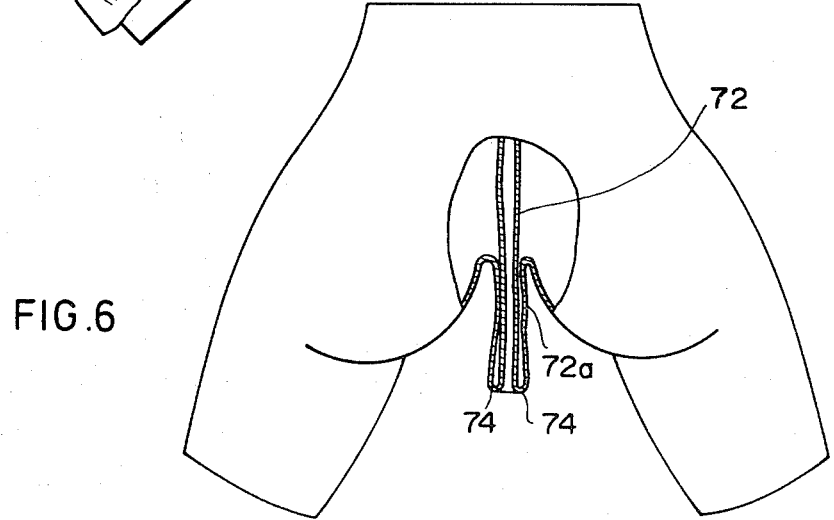
Figure 7:
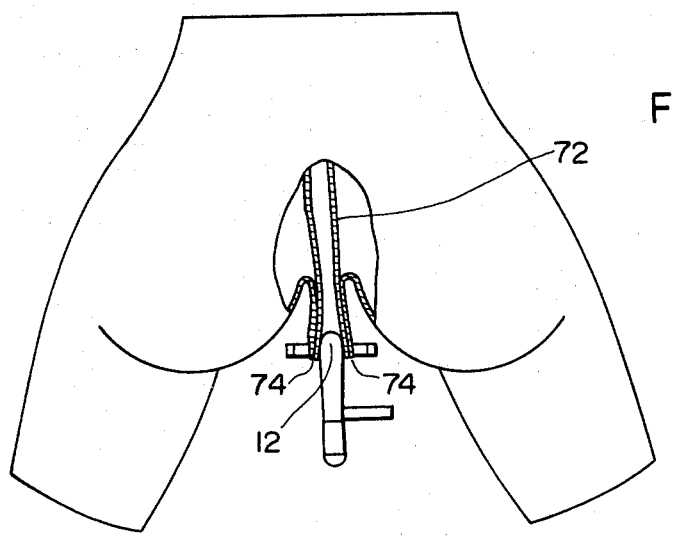
Figure 9:
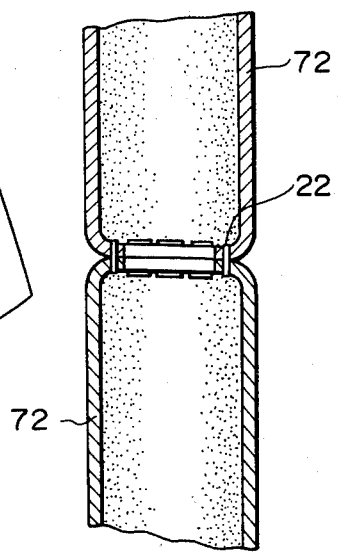
Figure 8:
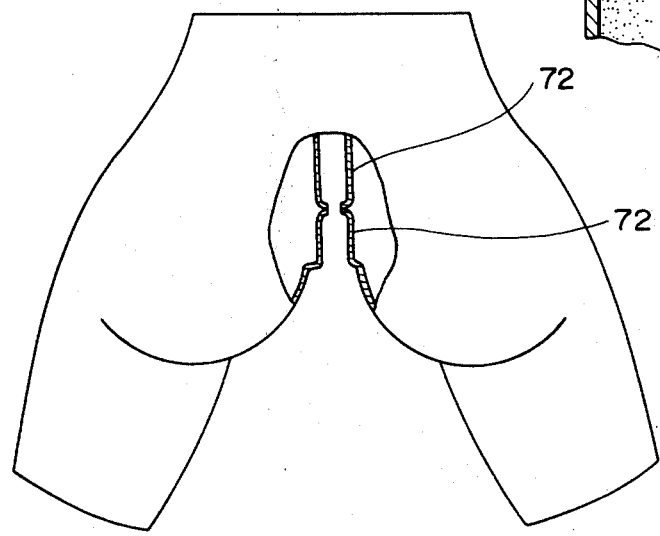

As shown in FIG. 6, a part 72a of the rectum 72 is pulled out from the anus in the reversed state, and the diseased part 74 thereof is positioned at the tip. Thereafter, as shown in FIG. 7, the nozzle tip 12 of the apparatus of the invention is inserted into the opening of the rectum 72 and then the needle opposing seats 14 and the suturing members 16 are positioned just above the diseased part 74 of rectum 72 to be cut off. The suturing member 16 is then approached to the needle seats 14 by operation of the actuating bars 28 for holding a part of the rectum 72 therebetween. Then, the operating member 26 is pushed inwardly so as to insert the pushing member 24 into the suturing member 16, thereby piercing the rectum 72 by the pushed out needle 22, tip edges of which are bent through contact with the needle opposing seats 14. Thus, the rectum 72 may be sutured. Upon completion of the suturing procedure, the suturing member 16 is moved apart from the rectum 72 and the apparatus is removed therefrom. After the diseased part is then cut off, the sutured rectum 72 is returned into the body, as shown in FIG. 8. The sutured rectum 72 after the operation is shown in FIG. 9.

In accordance with another embodiment of the cutting operation, the diseased part of the rectum 72 may previously be cut off by the laparotomy and thereafter the cut ends of the rectum 72 are pulled out from the body for being subjected to the suturing operation according to the invention.

As is apparent from the foregoing, in accordance with the apparatus of the invention, the rectum may be kept in the tubular state and may be sutured instantaneously and properly.

In accordance with the apparatus of the invention, further, the outer walls of the rectum to be sutured may be closely contacted with each other, so that the healing-up of the sutured part is very rapid and excellent.

In accordance with the apparatus, in particular, the nozzle tip to be inserted into the rectum is circular in section, so that the deformation of the rectum is very small upon insertion of the nozzle tip thereinto. Since the needle opposing seats may be uniformly arranged on the circumference of the round supporting member and the suturing member may be located annularly around the needle seats, the rectum may be uniformly and closely held between the needle seats and the suturing member, permitting very smooth suturing operation.

In accordance with the apparatus of the invention, moreover, a plurality of the pushing members provided for each suturing member may be slidably fitted to the operating member so as to freely vary the distance between the adjacent pushing members, so that the radial movement of the pushing members may be very smoothly achieved. In this connection, the apparatus of the invention may achieve the rapid and smooth suturing purpose. Finally, it is preferred to form the pushing member in a convex shape in section, as shown in FIG. 4a, for obtaining higher strength.

The foregoing detailed description has been given for clearness of understanding only and no unnecessary limitations are to be inferred therefrom.

What is claimed is:

1. An apparatus for suturing a doubled rectum which comprises a cylindrical hollow supporting member having at its one end a nozzle tip of a size and length to be inserted into the rectum, said nozzle tip having at its front end an aperture for washing the inside of the hollow supporting member and being provided with a plurality of needle opposing seats located behind the nozzle tip and on the circumference of the supporting member, four suturing members surrounding the needle opposing seats and annularly spaced apart from each other, said suturing members each having therein a plurality of needle receiving spaces extending radially and a plurality of pushing members slidably inserted into the needle receiving spaces for pushing needles toward the needle opposing seats, four actuating bars each being pivoted to the supporting member and connected at its one end to a said suturing member for allowing radial movement thereof in relation to the supporting member, an adjusting member provided at the other end of the supporting member for radially moving the actuating bars through a mechanism arranged within the supporting member, and four operating members each tangentially slidably receiving the outer ends of a said plurality of pushing members to move said pushing members radially.

2. An apparatus as claimed in claim 1 wherein the needle receiving spaces are arranged doubly within each suturing member.

3. An apparatus as claimed in claim 1, wherein the pushing member has an elongated hole into which is inserted a pin for slidably attaching the pushing member to the suturing member, and the outer edges of the pushing member are bent to form the bent parts which are slidably fitted into a dovetail groove of the operating member.

4. An apparatus as claimed in claim 1, wherein the actuating bar is pivoted at its other end to projected pieces of the supporting member by a pin and projections adjacent to the pivoted part of the actuating bar are fitted into a slot provided at one side of the supporting member for radially moving the actuating bar through a mechanism within the supporting member.

5. An apparatus as claimed in claim 1, wherein the adjusting member for moving the actuating bars is comprised of a knob provided at the other end of the supporting member, a threaded shaft connected to the knob and extended within the hollow supporting member, a moving member screwed onto the threaded shaft and located between projections of the actuating bar, which are fitted into a slot of the supporting member, and means restraining said moving member from rotation with the threaded shaft, whereby said moving member moves along the shaft when the knob is turned.

6. An apparatus as claimed in claim 1, wherein the needle is made from a single untwisted and unstranded stainless steel wire in the shape of a staple.

7. An apparatus as claimed in claim 1, wherein the supporting member is provided at its suitable part with a grip handle.

8. An apparatus as claimed in claim 1, wherein said nozzle tip forward of said needle opposing seats has a length greater than its diameter.

9. An apparatus as claimed in claim 8, wherein said nozzle tip terminates forwardly in a rounded end.

* * * * *